(12) United States Patent
Van Der Schuur et al.

(10) Patent No.: US 9,938,251 B2
(45) Date of Patent: Apr. 10, 2018

(54) CYCLIC KETONE PEROXIDE COMPOSITION

(71) Applicant: Akzo Nobel Chemicals International B.V., Arnhem (NL)

(72) Inventors: Jan Martijn Van Der Schuur, Hengelo (NL); Johan Nuysink, Rijssen (NL); Renaud Charles Joseph Millet, Gothenburg (SE); Bart Fischer, Leusden (NL)

(73) Assignee: AKZO NOBEL CHEMICALS INTERNATIONAL B.V., Arnhem (NL)

( * ) Notice: Subject to any disclaimer, the term of this patent is extended or adjusted under 35 U.S.C. 154(b) by 0 days.

(21) Appl. No.: 15/123,418

(22) PCT Filed: Mar. 9, 2015

(86) PCT No.: PCT/EP2015/054800
§ 371 (c)(1),
(2) Date: Sep. 2, 2016

(87) PCT Pub. No.: WO2015/135865
PCT Pub. Date: Sep. 17, 2015

(65) Prior Publication Data
US 2016/0368891 A1 Dec. 22, 2016

(30) Foreign Application Priority Data
Mar. 11, 2014 (EP) .................................. 14158878

(51) Int. Cl.
*C07D 323/00* (2006.01)
*C08K 5/14* (2006.01)
*C10L 1/18* (2006.01)

(52) U.S. Cl.
CPC .............. *C07D 323/00* (2013.01); *C08K 5/14* (2013.01); *C10L 1/1811* (2013.01)

(58) Field of Classification Search
CPC combination set(s) only.
See application file for complete search history.

(56) References Cited

U.S. PATENT DOCUMENTS

| 3,867,461 | A | 2/1975 | Leveskis et al. |
| 4,707,524 | A | 11/1987 | Ehrig et al. |
| 5,808,110 | A | 9/1998 | Torenbeek et al. |
| 6,358,435 | B1 | 3/2002 | Schuurman et al. |
| 6,844,408 | B2 | 1/2005 | Gonioukh et al. |
| 7,252,784 | B2 | 8/2007 | Fischer et al. |
| 7,456,212 | B2 | 11/2008 | Van Den Berg et al. |
| 2001/0034466 | A1 | 10/2001 | Deckers et al. |
| 2010/0324225 | A1 | 12/2010 | Zummallen |

FOREIGN PATENT DOCUMENTS

| GB | 912061 | | 12/1962 |
| GB | 1072728 | | 6/1967 |
| JP | 08107771 | A | 4/1996 |
| JP | 10-087652 | A | 4/1998 |
| JP | 2003213049 | A | 7/2003 |
| WO | 87/06944 | A1 | 11/1987 |
| WO | 93/25615 | A1 | 12/1993 |
| WO | 96/03397 | A1 | 2/1996 |
| WO | WO9603397 | * | 2/1996 |
| WO | 99/32584 | A1 | 7/1999 |
| WO | 00/23434 | A1 | 4/2000 |
| WO | 01/68723 | A2 | 9/2001 |
| WO | 2004/052877 | A1 | 6/2004 |
| WO | 2004/072059 | A1 | 8/2004 |

OTHER PUBLICATIONS

Search Report of corresponding EP Application No. 14158878.0, dated Sep. 16, 2014.
Search Report and Written Opinion of corresponding International Application No. PCT/EP2015/054800, dated Apr. 22, 2015.
Cafferata, et al., "Kinetics and Mechanism of Acetone Cyclic Diperoxide (3,3,6,6-Tetramethyl-1-1,2,4,5-tetraoxane) Thermal Decomposition in Benzene Solution," Institute de Investigaciones Fisicoquimicas Teoricas y Aplicadas, Inifta, Casila de Correo 16, Sucureal 4, 1900 La Plata, Argentina, Received Jul. 19, 1983, pp. 2107-2111.
Marino Xanthos, "Reactive Extrusion Principles and Practice," Polymer Processing Institute, 1992, pp. 34-41.
Eyler, et al., "Improved Procedure for the Preparation of Diethyl Ketone Triperoxide and Kinetics of Its Thermal Decomposition Reaction in Solution," Tetrahedron Letters, vol. 34, No. 11, 1993, pp. 1745-1746.

* cited by examiner

*Primary Examiner* — Prem C Singh
*Assistant Examiner* — Chantel Graham
(74) *Attorney, Agent, or Firm* — McDonnell Boehnen Hulbert & Berghoff LLP

(57) ABSTRACT

A composition comprising at least two trimeric cyclic ketone peroxides: a trimeric cyclic methyl ethyl ketone peroxide (3MEK-cp) of formula (I) and at least one peroxide satisfying formula (II) wherein $R^1$ through $R^3$ are independently selected from alkyl and alkoxyalkyl groups, said groups having 2 to 5 carbon atoms, the total number of carbon plus oxygen atoms of $R^1-R^2+R^3$ is in the range 7-15, and the molar ratio of 3MEK-cp to the total amount of peroxides satisfying formula (II) being in the range of from 10:90 to 80:20.

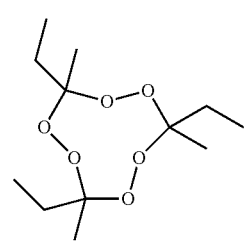

(I)

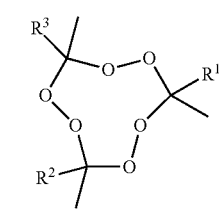

(II)

19 Claims, No Drawings

CYCLIC KETONE PEROXIDE COMPOSITION

This application is a national stage filing under 35 U.S.C. § 371 of PCT/EP2015/054800, filed Mar. 9, 2015, which claims priority to European Patent Application No. 14158878.0, filed Mar. 11, 2014, the contents of each of which are each incorporated herein by reference in their entirety.

The present invention relates to a composition containing cyclic ketone peroxides, a process for preparing such compositions, and the use of such compositions.

Compositions of cyclic peroxide ketones as such are known. For instance, WO 96/03397 discloses cyclic ketone peroxide compositions comprising one or more cyclic ketone peroxides and one or more diluents. However, the compositions that are disclosed pose a safety hazard when stored at 0° C. or below, due to the formation of explosive crystals. These crystals can explode spontaneously during storage and therefore pose a severe safety hazard. Although these safety issues could be resolved by strongly diluting the compositions of WO 96/03397, this would be highly undesired because that would result in compositions with too low active oxygen content, which would make these compositions inefficient in their application and would at the same time lead to unacceptable contamination of the polymers produced with these peroxide compositions.

WO 2004/072059 addresses the safety risks involved with crystallization of these type of peroxides and mitigates these risks by adding one or more dialkyl peroxides to the cyclic ketone peroxide composition. Dialkyl peroxides, however, are susceptible to static charges and therefore difficult to handle. They also pose potential health risks.

A further solution to the problem has been provided by WO 2004/052877, which adds a co-crystallizing compound, i.e. a compound that solidifies in the composition at a temperature above the crystallization temperature of the peroxide. An example of such a co-crystallizing compound is a paraffin wax. Unfortunately, such compositions are not suitable for use in all types of polymerization and (co) polymer modification processes. For example, in the production of low-density polyethylene (LDPE), the co-crystallizing compound solidifies under the high pressure reaction conditions that are applied, which may block the (peroxide dosing) conduits of the (tubular) reactor system that is used. Also, in most fields of use, the co-crystallizing compound ends up in the end-product and is typically seen as an undesired contaminant.

It is therefore an object of the present invention to overcome the above-described problems and improve the safety and storage stability of compositions containing cyclic ketone peroxides without requiring the addition of a co-crystallizing compound or dialkyl peroxide.

This object is met by providing a composition containing at least two trimeric cyclic ketone peroxides: a trimeric cyclic methyl ethyl ketone peroxide (3MEK-cp) of formula (I)

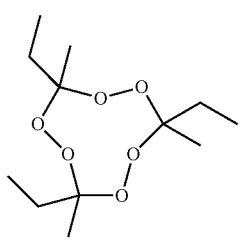

and at least one peroxide satisfying formula (II)

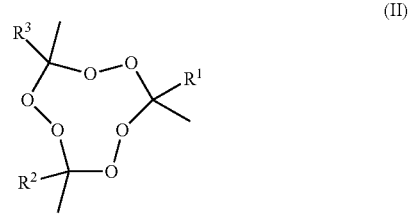

wherein $R^1$ through $R^3$ are independently selected from alkyl and alkoxyalkyl groups, said groups having 2 to 5 carbon atoms, the total number of carbon plus oxygen atoms of $R^1+R^2+R^3$ is in the range 7-15, and the molar ratio of 3MEK-cp to the total amount of peroxides satisfying formula (II) being in the range of from 10:90 to 80:20.

In this specification, the term alkoxyalkyl group refers to a group with the formula —$C_nH_{2n}$—O—$C_mH_{2m+1}$, wherein both n and m are at least 1. Because the total number of carbon atoms of said alkoxyalkyl group is in the range 2-5, n+m is in the range 2-5.

In a preferred embodiment, $R^1$ through $R^3$ are alkyl groups having 2 to 5 carbon atoms, the total number of carbon atoms of $R^1+R^2+R^3$ is in the range 7-15. In an even more preferred embodiment, said alkyl groups are linear alkyl groups.

In another preferred embodiment, the molar ratio of 3MEK-cp to the total amount of peroxides satisfying formula (II) is in the range of from 20:80 to 80:20, more preferably in the range of from 40:60 to 80:20, and most preferably in the range of from 50:50 to 80:20.

The amounts of the different peroxides in the composition can be analyzed by reversed phase HPLC using a C18 column and a water/acetonitrile gradient as mobile phase.

The composition according to the invention is considered safe if the crystallization point is below −5° C., preferably below −15° C., more preferably below −25° C., and most preferably below −40° C.

The crystallization point of the composition is determined as follows: first, the composition is cooled to a pre-determined temperature $T_1$. If, after 1 hour of stirring at $T_1$, crystals are formed in the composition, the composition is heated to a temperature ($T_2$) that is 3° C. higher than $T_1$. After stirring for about 6 hours, the composition is monitored to verify whether or not the crystals are dissolved. If not all crystals are dissolved, the temperature of the composition is raised another 3° C. and stirred at that temperature ($T_3$) for another 6 hours. These steps are repeated until a final temperature is reached at which all the crystals are dissolved. This final temperature is defined as the crystallization point of the composition. However, if no crystals are formed after 1 hour of stirring at $T_1$, a very small amount (at most 0.05%, based of the amount of cyclic ketone peroxide in the composition) of seeds of pure 3MEK-cp is added to the composition. After the addition of the seeds, the composition is stirred for 24 hours, after which it is again checked for the presence of crystals. If no crystals have formed, the temperature of the composition is decreased by 10° C. ($T_1$-10° C.) and seeded again. If crystals are formed after this temperature decrease, the temperature is raised at 3° C. intervals, according the above-described procedure, until all of the crystals are dissolved. However, if no crystals have formed, the temperature of the composition is decreased another 10° C. ($T_1$-20° C.) and another small amount of seeds is added to the formulation. The steps of the procedure are repeated (as described above) until the crystallization point of the composition is determined.

Preferably, at least one of the peroxides satisfying formula (II) is 3,6-diethyl-3,6,9-trimethyl-9-(n-propyl)-1,2,4,5,7,8-hexaoxonane (2MEK1MPK-cp). In an even more preferred embodiment, also 3-ethyl-3,6,9-trimethyl-6,9-di(n-propyl)-1,2,4,5,7,8-hexaoxonane (1MEK2MPK-cp) and/or 3,6,9-trimethyl-3,6,9-tri(n-propyl)-1,2,4,5,7,8-hexaoxonane (3MPK-cp) is/are present in the composition.

The composition according to the invention preferably contains a diluent. Examples of suitable diluents are linear and branched hydrocarbon solvents. Examples of such solvents are isododecane, tetradecane, tridecane, commercial mixtures of such hydrocarbons such as Isopar® M, Isopar® L, Spirdane® D60, Exxsol® D80, Exxsol® D100, Exxsol® D100S, Soltrol® 145, Soltrol® 170, Varsol® 80, Varsol® 110, Shellsol® D100, Shellsol® D70, and Halpasol® i 235/265, and mixtures thereof. Particularly preferred diluents are Isopar® M and Soltrol® 170. Examples of other suitable diluents can be found in U.S. Pat. No. 5,808,110. Although less preferred, it is also possible to use a specific fraction of the styrene oligomers disclosed in WO 93/25615.

Preferably, the composition of the present invention comprises at least 45 wt %, more preferably at least 50 wt %, and most preferably at least 55 wt % of diluent, and preferably at most 85 wt %, more preferably at most 80 wt %, and most preferably at most 75 wt % of diluent, based on the total weight of the composition.

The composition of the present invention may optionally contain certain additives, as long as these additives do not significantly suppress the safety, transportability and/or storage stability of the composition. Suitable examples of such additives are: antiozonants, antioxidants, antidegradants, UV stabilizers, coagents, fungicides, antistatic agents, pigments, dyes, coupling agents, dispersing aids, blowing agents, lubricants, process oils, and mould release agents. These additives may be employed in their conventional amounts. If used, such additives are typically added to the cyclic ketone peroxide composition shortly before the composition is used in a polymerization or (co)polymer modification process.

The total amount of trimeric cyclic ketone peroxides according to formulae (I) and (II) in the composition according to the present invention is preferably at least 15 wt %, more preferably at least 20 wt %, and most preferably at least 25 wt %, and preferably at most 55 wt %, more preferably at most 50 wt %, and most preferably at most 45 wt %.

There are two ways of preparing trimeric cyclic ketone peroxide compositions as described above. The first method involves the mixing of 3MEK-cp with the peroxide(s) satisfying formula (II).

The second method, which is the preferred method, involves the reaction of hydrogen peroxide with a mixture of ketones comprising methyl ethyl ketone (MEK) and at least one ketone of formula $CH_3—C(=O)—R$, wherein R is an alkyl group with 3 to 5 carbon atoms or an alkoxyalkyl group with 2 to 5 carbon atoms. This reaction requires the presence of acid.

This method has the advantage of requiring only one peroxide preparation reaction, instead of two.

Preferred ketones of formula $CH_3—C(=O)—R$ include methyl n-propyl ketone (R=n-propyl), methyl isopropyl ketone (R=isopropyl), methyl n-butyl ketone (R=n-butyl), methyl isobutyl ketone (R=isobutyl), methyl amyl ketone (R=n-pentyl), methyl isoamyl ketone (R=3-methylbutyl), and methoxyacetone (R=—$CH_2$—O—$CH_3$).

The most preferred ketone is methyl n-propyl ketone (R=n-propyl).

The molar ratio of methyl ethyl ketone to the total amount of ketones of formula $CH_3—C(=O)—R$ as defined above to be used in this process is preferably in the range 25:75 to 95:5, more preferably 30:70-70:30, even more preferably 40:60-70:30 and most preferably 50:50-70:30.

The reaction is preferably performed at a temperature in the range −5°-20° C., more preferably 0°-10° C. and most preferably 0-5° C. Higher temperatures promote the formation of dimeric cyclic ketone peroxides; lower temperatures slow down the reaction rate and increase the formation of linear peroxides.

The reaction is performed in the presence of an acid. This is preferably a strong acid. The most preferred acid is sulphuric acid. 78-85 wt % sulphuric acid solutions in water are preferred. Lower acid strength reduces conversion and reaction rate; higher acid strength may create safety problems and more by-products.

For safety reasons, it is highly desired to perform the reaction in the presence of a diluent. Suitable diluents are the ones listed above. The diluent is preferably mixed with the ketone mixture prior to the addition of acid and hydrogen peroxide.

The acid and hydrogen peroxide (separate or in admixture) are preferably slowly added to the ketone mixture. More preferably, they are dosed to said mixture within 30-90 minutes, even more preferably 40-80, minutes, most preferably 50-70 minutes.

After addition of the acid and hydrogen peroxide, the reaction mixture is preferably allowed to react for another at least 60, more preferably at least 70 minutes.

In addition to the peroxides of formulae (I) and (II), some linear as well as some dimeric cyclic structures may be formed in this reaction. This also means that the composition according to the present invention may contain some linear and/or dimeric cyclic ketone peroxides.

The peroxide composition according to the present invention can suitably be used as diesel additive, as cross-linking initiator, for initiating (radical) (co)polymerization reactions (e.g. high-pressure polymerization processes of ethylene to produce low-density polyethylene, styrene polymerizations and acrylate polymerizations) and (co)polymer modification processes (e.g. melt strength modification of polypropylene or polylactic acid and controlled rheology polypropylene (CR-PP) processing).

EXAMPLES

Example 1

In a 150 ml erlenmeyer $H_2SO_4$-78% (27.8 g) was added to $H_2O_2$-70% (22.8 g) at 0° C. (the premix). The premix was kept at 0° C. until needed.

A 300 ml reactor equipped with a turbine stirrer, was charged with Isopar M (38 g), methyl ethyl ketone (MEK; 24.7 g, 343 mmol), and methyl n-propyl ketone (MPK; 12.6 g, 147 mmol). The molar ratio of MEK to MPK was 70:30. The mixture was stirred (1200 rpm) and cooled down to 0° C. The premix was dosed to the mixture during a period of 60 min (0.650 ml/min) while keeping the temperature between −1° C. and +1° C. The reaction was kept at 0° C. for 75 min after dosing. The reaction was quenched by addition of water (13.8 g) and the phases were separated. The aqueous layer (bottom one) was removed.

HPLC showed the formation of the following compounds in the amounts listed in Table 1.

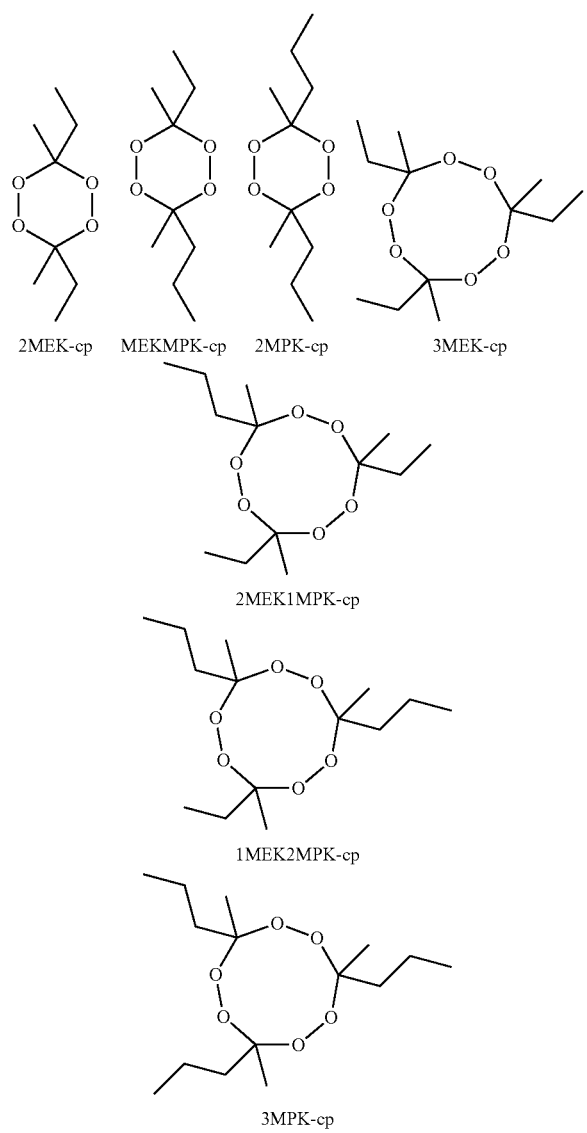

2MEK-cp    MEKMPK-cp    2MPK-cp    3MEK-cp

2MEK1MPK-cp

1MEK2MPK-cp

3MPK-cp

A sample from the composition was stored at −26° C. for 12 days in an isopropyl alcohol bath. After 5 days, the total active oxygen content (aO) was determined by way of a titration according to ASTM D2180-89(2008). This aO was compared with that of the fleshly prepared composition. Both before and after this storage period, the active oxygen content was 8 wt %, meaning that no significant peroxide decomposition occurred during storage.

After 12 days of storage, two samples were taken. One was analysed directly by HLPC; the other sample was allowed to reach room temperature (20° C.). The results are summarized in Table 1.

TABLE 1

| Component | Freshly prepared composition (wt %) | Mole ratio cyclic trimeric peroxides | Sample after 12 days at −26° C. (wt %) | Sample after 12 days at −26° C. then heated to 20° C. (wt %) |
|---|---|---|---|---|
| Isopar M | 50.3 | | 50.3 | 50.6 |
| MEK | 0.1 | | 0.1 | 0.1 |
| MPK | 1.5 | | 0.7 | 1.0 |
| 2MEK-cp | 2.3 | | 2.1 | 2.2 |
| MEKMPK-cp | 2.1 | | 2.0 | 2.0 |
| 2MPK-cp | 0.6 | | 0.6 | 0.6 |
| 3MEK-cp | 18.9 | 45.5 | 19.4 | 19.1 |
| 2MEK1MPK-cp | 17.6 | 40.2 | 18.1 | 17.8 |
| 1MEK2MPK-cp | 5.9 | 12.8 | 6.0 | 5.9 |
| 3MPK-cp | 0.7 | 1.5 | 0.7 | 0.7 |

No notable changes in the composition of the sample were observed, meaning that the composition was chemically stable under these conditions.

Example 2

Example 1 was repeated using MEK and MPK in different mole ratios and the crystallization temperatures of the freshly prepared compositions of Examples 1 and 2 were determined by the method described above.

All tests were performed in a test tube with a diameter of 28 mm. A sample of approx. 25 ml was poured into the test tube, the tube was closed tightly with a rubber stopper. The first temperature ($T_1$) was −15° C. As seeds, pure 3MEK-cp crystals were used.

TABLE 2

| MEK (mol %) | 100 | 50 | 70 | 75 | 80 |
|---|---|---|---|---|---|
| MPK (mol %) | 0 | 50 | 30 | 25 | 20 |
| Tcryst. (° C.) | 0° C. | −28 | <−28[1] | −16 | −15 |

[1] no crystallization observed at −28° C.

Example 3

Examples 1 and 2 were repeated using methyl isobutyl ketone (MiBK) instead of methyl n-propyl ketone. The results are listed in Table 3.

TABLE 3

| Ketone(s) other than MEK | mole ratio MEK:other ketone(s) | Tcryst. (° C.) |
|---|---|---|
| MPK | 50:50 | −28 |
| MiBK | 90:10 | −20 |
| MiBK | 50:50 | −23 |

Example 4

Examples 1 and 2 were repeated using of MEK, MPK, and methyl isopropyl ketone (MiPK) as the ketones, in a MEK:MPK:MiPK molar ratio of 70:15:15. The crystallization temperature of the resulting mixture was −23° C. and the composition of the mixture is shown in Table 4.

TABLE 4

| Component | Mole ratio cyclic trimeric peroxides |
|---|---|
| 3MEK-cp | 46.9 |
| 2MEK1MiPK-cp | 16.7 |
| 2MEK1MPK-cp | 24.3 |
| 1MEK2MiPK-cp | 1.7 |
| 1MEK1MPK1MiPK-cp | 5.4 |
| 1MEK2MPK-cp | 4.2 |
| 2MiPK1MPK-cp | 0.3 |
| 1MiPK2MPK-cp | 0.3 |
| 3MPK-cp | 0.2 |

Example 5

Examples 1 and 2 were repeated using of MEK, MPK, and MiBK as the ketones, in a MEK:MPK:MiBK molar ratio of 70:27:3.

Part of the resulting formulation was stored for three weeks at −40° C.; another part was stored for three weeks at room temperature.

No crystallization was observed in samples during this storage period. Nor did storage for one day at −44° C. or 2 days at −48° C. result in any crystallization. Also, no increase in explosive power was observed after storage at −40° C. compared to storage at room temperature. The explosive power was five times lower than that of a crystallized sample obtained from MEK as the only ketone stored at −15° C. (see table 2).

Example 6

The peroxide composition resulting from Example 1 was used to degrade polypropylene and its effectiveness was compared with that of commercial 41 wt % 3MEK-cp in Isopar M (Trigonox® 301).

Polypropylene (PP) degradation was performed at two different temperatures (190° C. and 225° C.) and at three different active oxygen contents (5.2 mg, 10.5 mg and 15.6 mg/100 g of PP).

Polypropylene (750 g) was extruded using a Polylab OS system fitted with a Haake PTW16 extruder (co-rotating twin screw). Temperature settings: hopper at 30° C., zone 1 at 160° C. and zones 2-10 at 225° C. or 190° C.

The melt flow index (MFI) of the degraded PP was measured and, as shown in Tables 5 and 6, it turned out that both peroxide compositions had the same efficiency in the degradation of PP, at all active oxygen contents and both temperatures. This shows that the composition according to the invention improves the safety of 3MEK-cp without impairing on efficiency.

TABLE 5

PP degradation at 190° C.

| | Active oxygen content (mg/100 g PP) | | |
|---|---|---|---|
| | 5.2 | 10.5 | 15.6 |
| | MFI at 230° C./2.16 kg (g/10 min): | | |
| Trigonox ® 301 | 16 | 40 | 75 |
| Example 1 | 16 | 41 | 74 |

TABLE 6

PP degradation at 225° C.

| | Active oxygen content (mg/100 g PP) | | |
|---|---|---|---|
| | 5.2 | 10.5 | 15.6 |
| | MFI at 230° C./2.16 kg (g/10 min): | | |
| Trigonox ® 301 | 14 | 38 | 72 |
| Example 1 | 14 | 37 | 77 |

The invention claimed is:

1. A composition comprising at least two trimeric cyclic ketone peroxides: a trimeric cyclic methyl ethyl ketone peroxide (3MEK-cp) of formula (I)

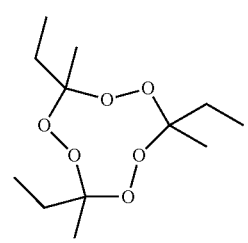

(I)

and at least one peroxide satisfying formula (II)

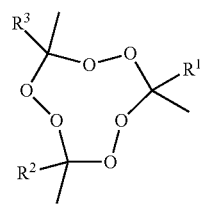

(II)

wherein $R^1$ through $R^3$ are independently selected from alkyl and alkoxyalkyl groups, said groups having 2 to 5 carbon atoms, the total number of carbon plus oxygen atoms of $R^1+R^2+R^3$ is in the range 7-15, and the molar ratio of 3MEK-cp to the total amount of peroxides satisfying formula (II) being in the range of from 10:90 to 80:20.

2. The composition according to claim 1 wherein $R^1$ through $R^3$ are alkyl groups having 2 to 5 carbon atoms, the total number of carbon atoms of $R^1+R^2+R^3$ is in the range 7-15.

3. The composition according to claim 2 wherein the alkyl groups are linear alkyl groups.

4. The composition according to claim 1 wherein the molar ratio of 3MEK-cp to the total amount of peroxides satisfying formula (II) is in the range of from 40:60 to 80:20.

5. The composition according to claim 1 wherein the composition further comprises a diluent in an amount of 45-85 wt %, based on the weight of the composition.

6. The composition according to claim 1 wherein the total amount of trimeric cyclic ketone peroxides according to formulae (I) and (II) is in the range 15-55 wt %, based on the weight of the composition.

7. The composition according to claim 1 wherein at least one of the peroxides satisfying formula (II) is 3,6-diethyl-3,6,9-trimethyl-9-(n-propyl)-1,2,4,5,7,8-hexaoxonane.

8. The composition according to claim 1 wherein at least one of the peroxides satisfying formula (II) is 3-ethyl-3,6,9-trimethyl-6,9-di(n-propyl)-1,2,4,5,7,8-hexaoxonane.

9. The composition according to claim 1 wherein at least one of the peroxides satisfying formula (II) is 3,6,9-tri(n-propyl)-3,6,9-trimethyl-1,2,4,5,7,8-hexaoxonane.

10. A process for preparing a cyclic ketone peroxide composition, the method comprising reacting, in the presence of acid, hydrogen peroxide with a mixture of ketones comprising methyl ethyl ketone (MEK) and at least one ketone of formula $CH_3$—C(=O)—R wherein R is an alkyl group with 3 to 5 carbon atoms or an alkoxyalkyl group with 2 to 5 carbon atoms, the molar ratio of MEK to the total amount of ketones of formula $CH_3$—C(=O)—R being in the range 25:75 to 95:5.

11. The process according to claim 10, wherein R is an alkyl group.

12. The process according to claim 11, wherein R is n-propyl.

13. The process according to claim 10, wherein the molar ratio of MEK to the total amount of ketones of formula $CH_3$—C(=O)—R is in the range of from 50:50 to 70:30.

14. A peroxide composition obtained by the process of claim 10.

15. The process of claim 13 wherein R is an alkyl group with 3 to 5 carbon atoms.

16. The process of claim 13 wherein R is n-propyl.

17. The peroxide composition of claim 14 wherein R is an alkyl group with 3 to 5 carbon atoms.

18. The peroxide composition of claim 14 wherein R is n-propyl.

19. The peroxide composition of claim 14 wherein the molar ratio of MEK to the total amount of ketones of formula $CH_3$—C(=O)—R is in the range of from 50:50 to 70:30.

* * * * *

UNITED STATES PATENT AND TRADEMARK OFFICE
CERTIFICATE OF CORRECTION

PATENT NO. : 9,938,251 B2
APPLICATION NO. : 15/123418
DATED : April 10, 2018
INVENTOR(S) : Van Der Schuur et al.

It is certified that error appears in the above-identified patent and that said Letters Patent is hereby corrected as shown below:

On the Title Page

Please amend the abstract, right-hand column as follows:
A composition comprising at least two trimeric cyclic ketone peroxides: a trimeric cyclic methyl ethyl ketone peroxide (3MEK-cp) of formula (I) and at least one peroxide satisfying formula (II) wherein R1 through R3 are independently selected from alkyl and alkoxyalkyl groups, said groups having 2 to 5 carbon atoms, the total number of carbon plus oxygen atoms of R1+R2+R3 is in the range 7-15, and the molar ratio of 3MEK-cp to the total amount of peroxides satisfying formula (II) being in the range of from 10:90 to 80:20.

Signed and Sealed this
Twenty-ninth Day of May, 2018

Andrei Iancu
*Director of the United States Patent and Trademark Office*